US007356367B2

(12) United States Patent
Liang et al.

(10) Patent No.: US 7,356,367 B2
(45) Date of Patent: Apr. 8, 2008

(54) COMPUTER AIDED TREATMENT PLANNING AND VISUALIZATION WITH IMAGE REGISTRATION AND FUSION

(75) Inventors: Zhengrong Liang, Stony Brook, NY (US); Dongqing Chen, Port Jefferson Station, NY (US); Bin Li, Centereach, NY (US); Clemente T. Roque, Stony Brook, NY (US); Eric E. Smouha, Northport, NY (US); Arie E. Kaufman, Plainview, NY (US); Mark R. Wax, Greenlawn, NY (US); Kevin Kreeger, E. Setauket, NY (US)

(73) Assignee: The Research Foundation of State University of New York, Stony Brook, NY (US)

( * ) Notice: Subject to any disclaimer, the term of this patent is extended or adjusted under 35 U.S.C. 154(b) by 870 days.

(21) Appl. No.: 10/297,349

(22) PCT Filed: Jun. 6, 2001

(86) PCT No.: PCT/US01/18353

§ 371 (c)(1), (2), (4) Date: Apr. 15, 2003

(87) PCT Pub. No.: WO01/93745

PCT Pub. Date: Dec. 13, 2001

(65) Prior Publication Data

US 2003/0208116 A1 Nov. 6, 2003

(51) Int. Cl.
*A61B 5/05* (2006.01)

(52) U.S. Cl. .................................................... 600/407
(58) Field of Classification Search ...................... None
See application file for complete search history.

(56) References Cited

U.S. PATENT DOCUMENTS 4,367,216 A    1/1983    Mutzel et al.

(Continued)

FOREIGN PATENT DOCUMENTS

| WO | 9613207 | 5/1996 |
|---|---|---|
| WO | 9811524 | 3/1998 |
| WO | 9837517 | 8/1998 |
| WO | 0055812 | 9/2000 |
| WO | 0055814 | 9/2000 |

OTHER PUBLICATIONS

Guillemaud et al. IEEE Transactions on Medical Imaging, vol. 16, No. 3, Jun. 1997.*

(Continued)

*Primary Examiner*—Brian L. Casler
*Assistant Examiner*—John F. Ramirez
(74) *Attorney, Agent, or Firm*—Dorsey & Whitney LLP

(57) ABSTRACT

A computer based system and method of visualizing a region using multiple image data sets is provided. The method includes acquiring first volumetric image data of a region and acquiring at least second volumetric image data of the region. The first image data is generally selected such that the structural features of the region are readily visualized. At least one control point is determined in the region using an identifiable structural characteristic discernable in the first volumetric image data. The at least one control point is also located in the at least second image data of the region such that the first image data and the at least second image data can be registered to one another using the at least one control point. Once the image data sets are registered, the registered first image data and at least second image data can be fused into a common display data set. The multiple image data sets have different and complimentary information to differentiate the structures and the functions in the region such that image segmentation algorithms and user interactive editing tools can be applied to obtain 3d spatial relations of the components in the region. Methods to correct spatial inhomogeneity in MR image data is also provided.

23 Claims, 10 Drawing Sheets

U.S. PATENT DOCUMENTS

| | | | |
|---|---|---|---|
| 4,391,280 | A | 7/1983 | Miller |
| 4,630,203 | A | 12/1986 | Szirtes |
| 4,710,876 | A | 12/1987 | Cline et al. |
| 4,719,585 | A | 1/1988 | Cline et al. |
| 4,729,098 | A | 3/1988 | Cline et al. |
| 4,737,921 | A | 4/1988 | Goldwasser et al. |
| 4,751,643 | A | 6/1988 | Lorensen et al. |
| 4,791,567 | A | 12/1988 | Cline et al. |
| 4,823,129 | A | 4/1989 | Nelson |
| 4,831,528 | A | 5/1989 | Crawford et al. |
| 4,874,362 | A | 10/1989 | Wiest et al. |
| 4,879,668 | A | 11/1989 | Cline et al. |
| 4,984,157 | A | 1/1991 | Cline et al. |
| 4,985,834 | A | 1/1991 | Cline et al. |
| 4,985,856 | A | 1/1991 | Kaufman |
| 4,987,554 | A | 1/1991 | Kaufman |
| 4,993,415 | A | 2/1991 | Long |
| 5,006,109 | A | 4/1991 | Douglas et al. |
| 5,023,072 | A | 6/1991 | Cheng |
| 5,038,302 | A | 8/1991 | Kaufman |
| 5,047,772 | A | 9/1991 | Ribner |
| 5,056,020 | A | 10/1991 | Feldman et al. |
| 5,095,521 | A | 3/1992 | Trousset et al. |
| 5,101,475 | A | 3/1992 | Kaufman |
| 5,127,037 | A | 6/1992 | Bynum |
| 5,166,876 | A | 11/1992 | Cline et al. |
| 5,170,347 | A | 12/1992 | Tuy et al. |
| 5,187,658 | A | 2/1993 | Cline et al. |
| 5,204,625 | A | 4/1993 | Cline et al. |
| 5,229,935 | A | 7/1993 | Yamagishi et al. |
| 5,245,538 | A | 9/1993 | Lis |
| 5,261,404 | A | 11/1993 | Mick et al. |
| 5,265,012 | A | 11/1993 | Amans et al. |
| 5,270,926 | A | 12/1993 | Tam |
| 5,283,837 | A | 2/1994 | Wood |
| 5,295,488 | A | 3/1994 | Lloyd et al. |
| 5,299,288 | A | 3/1994 | Glassman et al. |
| 5,322,070 | A | 6/1994 | Goodman et al. |
| 5,345,490 | A | 9/1994 | Finnigan et al. |
| 5,361,763 | A | 11/1994 | Kao et al. |
| 5,365,927 | A | 11/1994 | Roemer et al. |
| 5,371,778 | A | 12/1994 | Yanof et al. |
| 5,442,733 | A | 8/1995 | Kaufman et al. |
| 5,458,111 | A | 10/1995 | Coin |
| 5,611,025 | A | 3/1997 | Lorensen et al. |
| 5,623,586 | A | 4/1997 | Höhne |
| 5,630,034 | A | 5/1997 | Oikawa et al. |
| 5,699,799 | A | 12/1997 | Xu et al. |
| 5,734,384 | A | 3/1998 | Yanof et al. |
| 5,782,762 | A | 7/1998 | Vining |
| 5,971,767 | A | 10/1999 | Kaufman |
| 5,986,662 | A | 11/1999 | Argiro et al. |
| 6,130,671 | A | 10/2000 | Argiro |
| 6,219,059 | B1 | 4/2001 | Argiro |
| 6,272,366 | B1 | 8/2001 | Vining |
| 2001/0055016 | A1 | 12/2001 | Krishnan |
| 2002/0164061 | A1 | 11/2002 | Paik et al. |

OTHER PUBLICATIONS

Jensch et al. Computers in Cardiology 1990. Proceedings. Sep. 1990:307-310.*

Chen et al. IEEE Transactions on Medical Imaging, vol. 19, No. 4, Apr. 2000.*

Hastreiter et al. Computer Graphics International, 1998. Proceedings. Jun. 22-26, 1998 pp. 78-85.*

Hong et al., "3D Virtual Colonoscopy," 1995 Biomedical Visualization Proceedings, pp. 26-32 and 83 (1995).

Hong et al., "3D Reconstruction and Visualization of the Inner Surface of the Colon from Spiral CT Data," IEEE, pp. 1506-1510 (1997).

William E. Lorensen, "The Exploration of Cross-Sectional Data with a Virtual Endoscope," Interactive Technology and the New Health Paradigm, IOS Press, pp. 221-230 (1995).

Adam L. Penenberg, "From Stony Brook, a New Way to Examine Colons, Externally," The New York Times, p. 6 (1996).

David J. Vining, "Virtual Colonoscopy," Advance for Administrators in Radiology, pp. 50-52 (1998).

Zhou et al., "Three-Dimensional Skeleton and Centerline Generation Based on an Approximate Minimum Distance Field," The Visual Computer, 14:303-314 (1998).

Liang Z et al., "Inclusion of a priori information in segmentation of colon lumen for 3D virtual colonscopy", 1997 IEEE Nuclear Science Symposium Conference Record, pp. 1423-1427, vol. 2.

Valev et al., "Techniques of CT colongraphy (virtual colonoscopy)", Critical Reviews in Biomedical Engineering, 1999, Begall House, vol. 27, No. 1-2, pp. 1-25.

Shibolet O et al., "Coloring voxel-based objects for virtual endoscopy", IEEE Symposium on Volume Visualization, Research Triangle, Oct. 1998.

Kaufman A., Wan M., "Disobstruction of Colon Wall Collapse", Project Description, online www.cs.sunysb.edu, Jan. 1999.

Holzapfel G A, et al., "Large strain analysis of soft biological membranes: formulation and finite element analysis", Computer Methods in Applied Mechanics and Engineering, vol. 132, No. 1-2, pp. 45-61, 1996.

Kaye J. et al., "A 3D virtual environment for modeling mechanical cardiopulmonary interactings", CVRMED-MRCAS '97, pp. 389-398, 1997.

Burgard W. et al., "Active mobile robot localization by entrophy minimization", Proceedings second euromicro workshop on advanced mobile robots, pp. 155-162, 1997.

Suya You et al., "Interactive volume rendering for virtual colonoscopy", Proceedings Visualization '97, pp. 433-436, 571.

Pai D.K. et al., "Multiresolution Rough Terrain Motion Planning", IEEE Transactions on Robotics and Automatic, vol. 14, No. 1, pp. 19-33, 1998.

Hagen H. et al., "Methods for Surface Interrogation", Proceedings of the Conference on Visualization, vol. CONF 1, pp. 187-193, 1990.

Chen et al., "A tree-branch searching, multiresolution approach to skeletonization for virtual endoscopy", unable to identify date.

Liang Z. et al., "Feasibility Studies on Extracting Bladder Wall from MR Images for Virtual Cystoscopy", unable to identify date.

Chen et al., "Virtual Laryngoscopy: Feasibility Studies by CT and MRI", IEEE Medical Imaging Conference, Nov. 1999.

Chen et al., A multi-scan MRI-based virtual cystoscopy, unable to identify date.

Chen et al., "MRI-Based Virtual Cystoscopy: The image segmentation and visualization", SPIE Conference, Feb. 12-18, 2000.

Chen et al., "A Fast Algorithm to Generate Centerline for Virtual Colonscopy", SPIE Conference, Feb. 12-18, 2000.

Richard Robb, "Virtual (Computed) Endoscopy: Development and Evaluation Using the Visible Human Datasets", Oct. 7-8, 1996. www.mayo.edu.

I. Bitter et al., "Penallized-Distance Volumetric Skeleton Algorithm", IEEE Transactions on Visualization and Computer Graphics, vol. 7, No. 3, Jul.-Sep. 2001, pp. 195-206.

M. Wan et al., "Distance-Field Based Skeletons for Virtual Navigation", *Visualization 2001*, San Diego, CA, Oct. 2001.

M. Sato et al., "An automatic colon segmentation for 3D virtual colonoscopy", IEICE Trans. Information and Systems, vol. E84-D, No. 1, Jan. 2001, pp. 201-208.

D. Chen et al., "A Novel Approach to Extract Colon Lumen from CT Images for Virtual Colonoscopy" IEEE Transactions on Medical Imaging, vol. 19, No. 12, Dec. 2000, pp. 1220-1226.

M. Wax et al., "Virtual Colonoscopy—CT Contrast Agent", Second International Symposium on Virtual Colonoscopy, Boston, MA, Oct. 2000.

K. Kreeger, et al., "Volume Rendering for Virtual Colonoscopy on an Affordable PC", Second International Symposium on Virtual Colonoscopy, Boston, MA, Oct. 2000.

S. Lakare et al., "3D Digital Cleansing Using Segmentation Rays", IEEE Visualization 2000 Conference Proceedings, ACM/SIGGRAPH Press, pp. 37-44, Oct. 2000.

S. Lakare et al., "Automated Pre-navigation processing for Virtual Colonoscopy", Second International Symposium on Virtual Colonoscopy, pp., Oct. 2000.

K. Kreeger et al., "Perspective Virtual Endoscopy with VolumePro Parallel Rendering", Center for Visual Computing and Department of Computer Science, pp. 1-8, unable to identify date.

D. Chen et al. "A tree-branch searching, multi-resolution approach to skeletonization for virtual endoscopy", SPIE Medical Imaging 2000, Feb. 2000.

M. Wan et al., "3D Virtual Colonoscopy with Real-time Volume Rendering", SPIE Medical Imaging 2000, Feb. 2000.

M. Wax et al., "Advancing Virtural Colonoscopy to Practice", International Workshop on 3D Imaging and Virtual Endoscopy, Feb. 2000.

W. Li et al., "Virtual Colonoscopy Powered by VolumePro", pp. 1-13, month unavailable 1999.

M. Wan et al., "Volume Rendering Based Interactive Navigation within the Human Colon", IEEE Visualization '99 conference, San Francisco, CA, Oct. 1999, pp. 397-400.

R. Chiou et al., "Interactive Fly-Path Planning Using Potential Fields and Cell Decomposition for Virtual Endoscopy", IEEE Trans. Nuclear Sciences, vol. 46, No. 4, Aug. 1999, pp. 1045-1049.

D. Chen et al., "MR Imaging and Segmentation of the Colon Wall for Virtual Colonoscopy", Soc. Magn. Reson. Medicine, vol. 3, pp. 2203, unable to identify date.

R. Chiou et al., "Volume Segmentation and Rendering of Mixtures of Materials for Virtual Colonoscopy", SPIE Medical Imaging '99, Feb. 1999, pp. 133-138.

Z. Liang et al., "On Segmentation of Colon Lumen for Virtual Colonoscopy", SPIE Medical Imaging, Feb. 1999, pp. 270-278.

Z. Liang et al., "Virtual Endoscopy in Early Detection of Cancers", Biomedical Imaging Symposium: Visualizing the Future of Biology and Medicine, Washington, D.C., Feb. 1999.

R. Chiou et al., "Unified Analysis, Modeling, Matching and Synthesis for CT Color Texture Mapping from the Visible Human Dataset", The Second Visible Human Project Conf., Bethesda, MD, Oct. 1998.

M. Wan et al., "Boundary Cell-Based Acceleration for Volume Ray Casting", Computer & Graphices, vol. 22, No. 6, 1998, pp. 715-721.

R. Chiou et al., "Interactive Path Planning for Virtual Endoscopy", Conf. Record IEEE NSS-MIC, Nov. 1998.

M. Wax et al., "Electronic Colon Cleansing for Virtual Colonoscopy", Presentation at the first Int'l. Conf. on Virtual Colonoscopy, Boston, MA, Oct. 1998.

L. Hong et al., "Virtual Voyage: Interactive Navigation in the Human Colon", Proc. ACM SIGGRAPH '97, Aug. 1997, pp. 27-34.

A. Viswambharan et al., "Virtual Colonoscopy: Three-dimensional Reconstruction of the Mucosal Surface of the Colon", Conf. of Radiological Society of North America (RSNA), Dec. 1996, pp. 565 (Scientific Merit Award).

L. Hong et al., "Physcially-Based Interactive Navigation", Technical Report TR.96.01.09, Computer Science Department, SUNY at Stony Brook, Jan. 1996.

L. Hong et al., "Visible Human Virtual Colonoscopy", Conference of National Library of Medicine Visible Human Project, Oct. 1996, pp. 29-30.

80th Scientific Assembly and Annual Meeting Nov. 27-Dec. 2, 1994, Radiology Society of North America Founded in, InfoRAD Exhibits.

Taosong He, et al. "Collision Detection for Volumetric Objects", Proceedings of the 8th IEEE Visualization Conference, 1997 1070-2385/97.

Yaoping Wang et al., "Real-Time Interactive Simulator for Percutaneous Coronary Revascularization Procedures", Computer Aided Surgery, 3:211-227, 1998.

Pending application with common assignee and potentially related subject matter—U.S. Appl. No. 11/613,306, filed Dec. 20, 2006.

Pending application with common assignee and potentially related subject matter—U.S. Appl. No. 10/182,217, filed Feb. 19, 2003.

Pending application with common assignee and potentially related subject matter—U.S. Appl. No. 10/297,349, filed Apr. 15, 2003.

Pending application with common assignee and potentially related subject matter—U.S. Appl. No. 10/380,211, filed Feb. 2, 2004.

Pending application with common assignee and potentially related subject matter—U.S. Appl. No. 10/246,070, filed Sep. 16, 2002.

Pending application with common assignee and potentially related subject matter—U.S. Appl. No. 10/246,015, filed Sep. 16, 2002.

Pending application with common assignee and potentially related subject matter—U.S. Appl. No. 10/380,210, filed Sep. 6, 2005.

* cited by examiner

COMPUTER AIDED TREATMENT PLANNING AND VISUALIZATION WITH IMAGE REGISTRATION AND FUSION

GOVERNMENT INTERESTS

The invention disclosed herein was made with Government support under NIH Grant CA 79180. Accordingly, the U.S. Government may have certain rights in this invention.

FIELD OF THE INVENTION

The present invention relates generally to surgical planning and more particularly relates to systems and methods of registering, segmenting and analyzing image data for three dimensional interactive computer visualization and surgical planning and follow-up evaluation.

BACKGROUND OF THE INVENTION

In many areas of medical treatment, it would be beneficial for a medical practitioner to be able to visualize a region for which treatment is contemplated and to accurately simulate the contemplated treatment. By visualizing the effect of the simulated treatment and altering the proposed treatment to optimize the results in a virtual setting, results can be improved and risks associated with the actual treatment can be reduced. This is particularly true in the case of invasive procedures such as surgery, biopsies and prosthesis implantation. The virtual setting would serve both as a tool for the guidance for actual treatment and as a "gold standard" for evaluation of the actual treatment and for follow-up management. Such a system can also provide an intuitive tool for medical training.

Preoperative imaging, such as by computerized tomography (CT), magnetic resonance imaging (MRI), ultrasound (US) and the like, is considered an important element in surgical planning. These conventional imaging technologies provide two dimensional (2D) image slices which illustrate key anatomic structures in a region of interest. However, the 2D slice images are limited in their ability to represent the spatial relationships between adjacent and interrelated structures. For example, a retro-displaced bifurcation point of carotid arteries might make stenosis analysis and plaque removal planning difficult. Three-dimensional (3D) information would be very helpful for planning surgical therapy.

Traditionally, spatial anatomical relationships could only be surmised by mentally integrating sequential 2D slice images. However, the advent of 3D computer graphical visualization techniques and high-resolution image scanning now allow 3D images (either surface-based or volume-based) to be constructed from sequential slice images and be displayed on a computer screen. Three-dimensional relationships between adjacent organs can be shown by interactively manipulating these virtual organs on the screen using a mouse or some other interactive devices. Over the past decade, many applications of such techniques in a number of areas of medicine, including otology, and neurology have been explored.

To achieve more accurate tissue classification and insight regarding tissue functionality, a series of single modality images and multi-modality images can be utilized. The single modality images can be of a common region acquired at different times or different orientations. In multi-modality images, the same region is imaged using two or more imaging technologies, such as CT, MRI and US in order to take advantage of the properties of each technology since a certain modality image may be sensitive to certain kind of tissues or their functions. By using single modality image series and multi-modality images, more information can be obtained, and limitations of certain modality can be mitigated.

The use of multiple image sets (including multi-modality images and or single modality image series) would be useful to perform virtual visualization and treatment planning for carotid artery stenosis and other conditions. Carotid artery stenosis is the most common cause of stroke, which is a major health care problem, that affects more than 700,000 Americans each year. In fact, this condition is the leading cause of disability and the third leading cause of deaths in the United States, after cardiovascular disease and cancer. Stenosis arises from the formation of plaque (consisting of calcification, cholesterol, and blood elements). The surgical procedure to remove plaque from a neck artery is called carotid endarterectomy. Prior to endarterectomy, the degree of stenosis needs to be measured and the position of the plaque must be localized. Currently available methods for evaluating carotid stenosis include, for example, carotid Doppler ultrasound and contrast angiography, which have been demonstrated for accurate determination of the degree of luminal stenosis. However, luminal narrowing is an indirect marker of plaque size and may underestimate the plaque burden as plaque may grow inside the vessel wall from the lumen towards the outer surrounding tissues. It is desirable that plaque size (both inwards and outwards boundary) and composition are accurately measured. These measures are of value since both plaque rupture and plaque removal carry risk. The measures relating to plaque composition and the likelihood of rupture can offer valuable risk assessment for the decision whether or not to proceed with a plaque removal operation.

Currently, MR data, CT data and US data each provide some insight into the structure, nature and position of stenosis within an artery. However, neither imaging technology alone is sufficient to provide a complete analysis of the size, composition and position of the plaque buildup. The benefits of these imaging technologies are largely complimentary and there would be a great benefit in having the ability to readily register images of a region using these complimentary technologies and to fuse the images into a single display. There is also a benefit in having the ability to register and fuse a series of single mode images to capture complimentary information contained therein.

In MR image data, the inter-slice and even intra slice image data often contains spatial inhomogeneity which adversely affects automated analysis of these images. Correction for spatial intensity inhomogeneities in inter- and intra-slices provides improved results in automated quantitative analysis of MR images. The inhomogeneities locally alter image intensity mean, median, and variance. It is known that they vary over time and with different acquisition parameters and subjects. For virtual treatment planning, a general purpose correction algorithm that can work for any scanning protocol and anatomy region is desirable. The concept of correcting image artifacts can be applied to the beam-hardening problem encountered in CT images as well as the attenuation distortion in US images.

Accordingly, there remains a need for improved medical treatment planning tools for optimizing the procedures and for evaluating the results.

SUMMARY OF THE INVENTION

It is an object of the present invention to provide a method of flexible image registration suitable for use in three dimensional (3D) visualization systems.

It is a further object of the present invention to provide a method of visualizing a region using multiple image sets, such as a set of single-modality images or multi-modality images, in a manner where complimentary image data properties can be fused in a common, registered display.

In accordance with one embodiment of the present method, a computer based method of visualizing a region using multiple image data sets is provided. The method includes acquiring first volumetric image data of a region and acquiring at least second volumetric image data of the region. The first image data is generally selected such that the structural features of the region are readily visualized. At least one control point is determined in the region using an identifiable structural characteristic discernable in the first volumetric image data. The at least one control point is also located in the at least second image data of the region such that the first image data and the at least second image data can be registered to one another using the at least one control point. Once the image data sets are registered, the registered first image data and at least second image data can be fused into a common display data set.

The method can be used in connection with the visualization of branched structures, such as arterial structures. In this case, a bifurcation point in the arterial structure can be selected as the control point.

The first image data and the additional sets of image data can be of the same region at different times, of the same region with different patient orientations, or of the same region using different imaging modes. The various sets of images, either single-modality image sets or multi-modality images, are selected to provide complimentary imaging characteristics. For example, in the case of visualizing an arterial structure for carotid stenosis, a first imaging mode can be used to delineate the arterial lumen, a second imaging mode can be used to delineate fatty components of plaque deposits and third imaging mode can be used to delineate calcification components of plaque deposits.

A method is also provided for correcting spatial inhomogenieties which may occur in MR image data. After acquiring the MR image data, a bias field associated with the image data is estimated. The bias field is then applied to the MRI data to correct for the spatial inhomogenieties.

A method is also provided to assist a user, such as a physician, in editing the computer-aided, automatically processed results of a visualization, such as the segmentation of the tissues within the region from the multiple image sets. The user employs a graphical user interface to introduce editing to the multiple image sets. Such editing can also be used to manually optimize the registration and fusion operations for the multiple image sets.

BRIEF DESCRIPTION OF THE DRAWING

Further objects, features and advantages of the invention will become apparent from the following detailed description taken in conjunction with the accompanying figures showing illustrative embodiments of the invention, in which.

Figure 1:
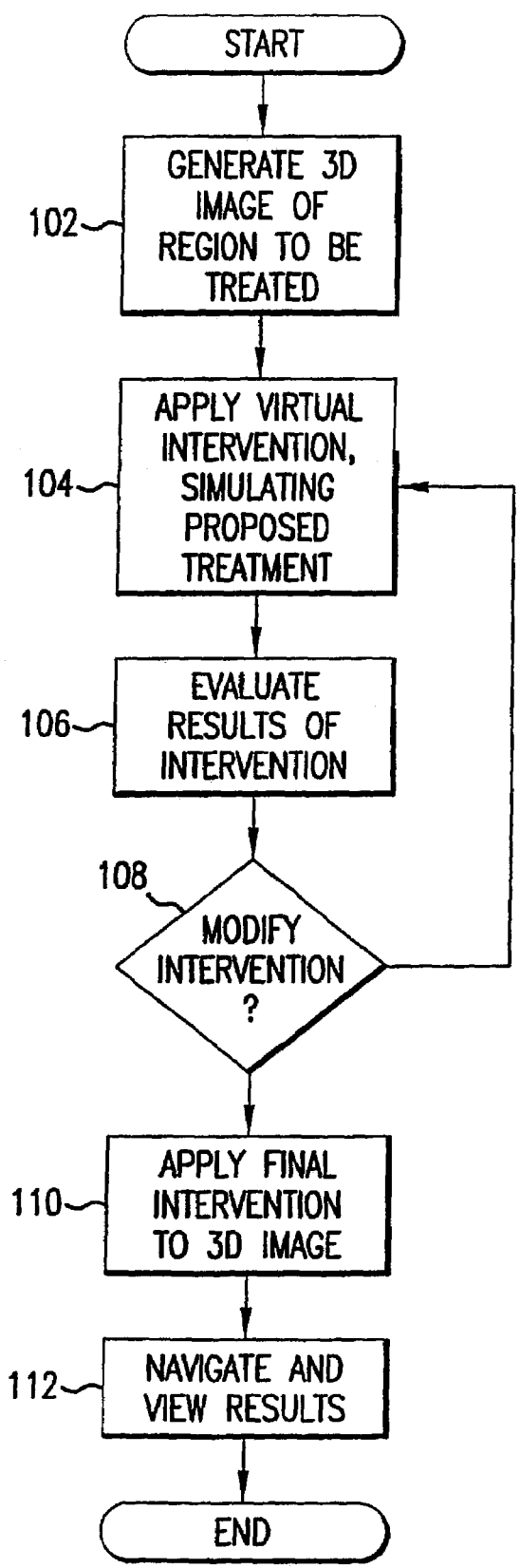
FIG. 1 is a simplified flow diagram illustrating an overview of a method for computer aided treatment planning and interactive visualization.

Throughout the figures, the same reference numerals and characters, unless otherwise stated, are used to denote like features, elements, components or portions of the illustrated embodiments. Moreover, while the subject invention will now be described in detail with reference to the figures, it is done so in connection with the illustrative embodiments. It is intended that changes and modifications can be made to the described embodiments without departing from the true scope and spirit of the subject invention as defined by the appended claims.

DETAILED DESCRIPTION OF PREFERRED EMBODIMENTS

Figure 2:
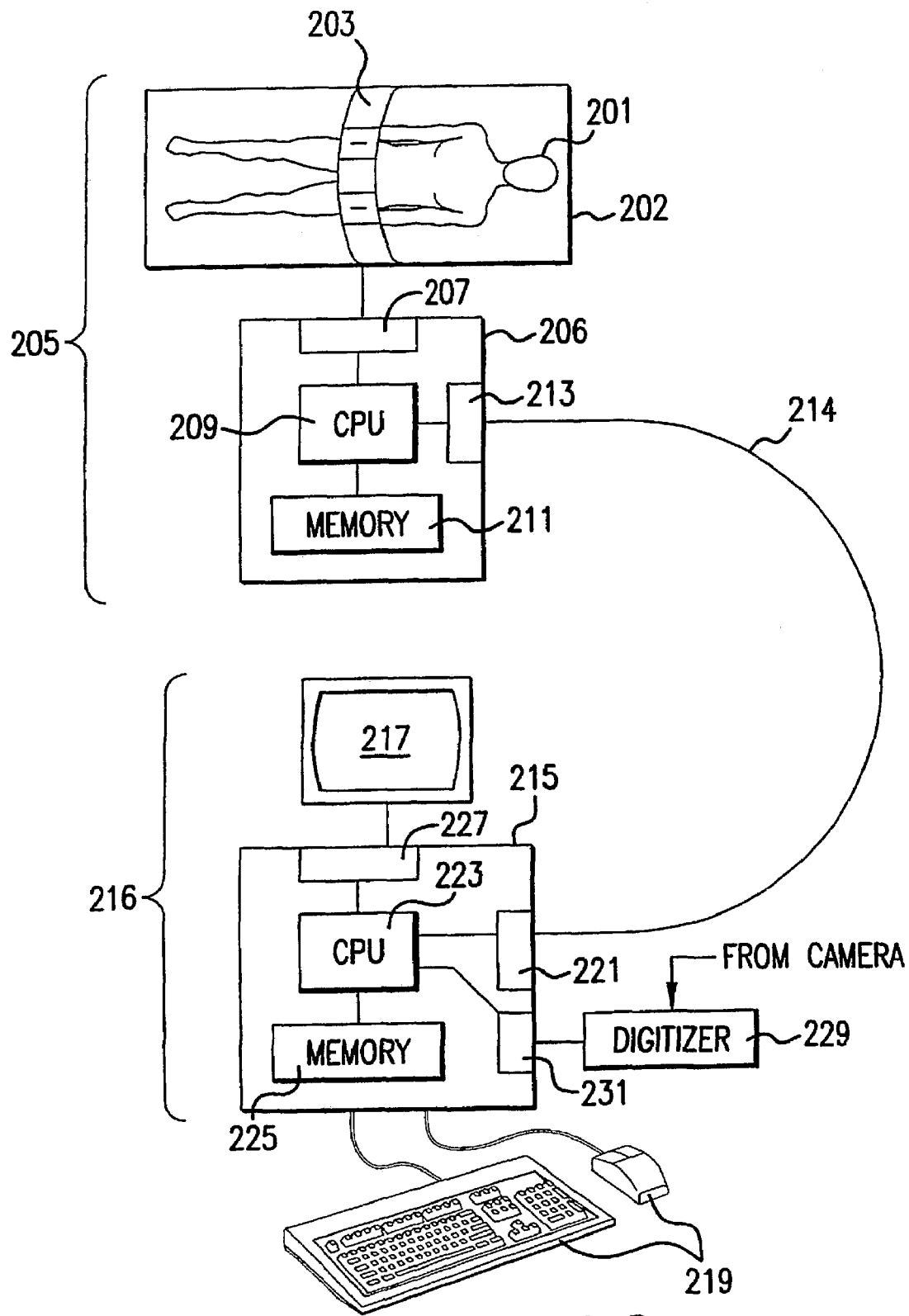
FIG. 2 is a simplified block diagram of a system suitable for performing the present method of computer aided treatment planning and interactive visualization.

FIG. 1 is a flow chart which illustrates an overview of the present method of computer aided treatment planning and interactive visualization which is generally performed on a computer based system, such as that illustrated in FIG. 2. The invention will be described in terms of medical applications performed on human patients and in the context of medical treatment, such as examination (e.g., measuring carotid stenosis and quantifying plaque components), surgery (e.g., removal of carotid plaque), prosthesis implantation, biopsy, medication, therapeutic radiation, therapeutic ultrasound and the like. It will be appreciated, however, that the invention is not limited to human patients, nor to the exemplary list of treatments referenced. The term treatment is used to mean an intervention in a region, such as but not limited to tissue, that is intended to effect an alteration of the region.

Referring to FIG. 1, the method includes the initial step of generating a three dimensional (3D) image representation of a region for which some form of medical treatment or intervention is contemplated (step 102). Generating such a 3D image representation generally involves acquiring a sequential series of 2D slice images, such as from a spiral computed tomography (CT) scanner, magnetic resonance imaging (MRI) scanner or ultrasound scanner (US) and transforming this 2D image data into a volumetric data set which provides a 3D representation of the region on a 2D display, such as a computer monitor. Such a technique is well known in the art, and is discussed, for example in U.S. Pat. No. 5,971,767 to Kaufman et. al., which is hereby incorporated by reference in its entirety.

After the 3D image is presented to a user, such as a physician, some form of virtual intervention, which simulates at least a portion of a proposed treatment, is applied to the 3D image (step 104). The virtual intervention can take on several forms, such as the quantifying of arterial stenosis and plaque components, removal of tissue or artery plaques, the repair or reconstruction of a diseased or malformed organ (e.g., inner ear, lungs, liver, joints, etc.), the placement of a prosthetic implant, the placement of a stent graft, the placement of biopsy needle, the placement of therapeutic radiation and the like.

Using the resulting 3D image, and possibly the assistance of computer generated models of the applied intervention, the results of the virtual intervention can be evaluated and warnings can be generated indicative of high levels of risk attendant with the proposed intervention (step 106). Based on the displayed results, and any warnings provided, the user can repeatedly modify the proposed intervention (step 108) and apply the modified intervention to the 3D image (step 104) until a satisfactory result is ascertained or it is determined that the proposed treatment is not feasible. Several alternative interventions can be saved in a database to compare the risks and efficacy of proposed alternative intervention plans. The quantified arterial stenosis and plaque components will provide a measure of risk factor for plaque rupture, which can result in stroke, pulmonary embolism, and occlusions in the liver and kidneys.

After the proposed intervention is finalized, the final intervention can be simulated and the results fully applied to the 3D image (step 110). The user can then view the results and navigate in and around the region to determine the efficacy of the proposed treatment (step 112). The planned results can then be used as a guide for the actual treatment with coordinate registration between the virtual model and the patient and as a gold standard to evaluate the actual intervention during post-intervention follow up examinations.

FIG. 2 is a simplified diagram of an exemplary system for performing the present computer aided treatment planning and interactive visualization methods. In this exemplary embodiment, a patient 201 lies down on a platform 202 while scanning device 205 scans the area that contains the organ or organs which are to be examined. The scanning device 205 contains a scanning portion 203 which acquires image data of the patient and an electronics portion 206. Electronics portion 206 generally includes an interface 207, a central processing unit 209, a memory 211 for temporarily storing the scanning data, and a second interface 213 for sending data to the virtual navigation platform. Interface 207 and 213 can be included in a single interface component or can even be the same component. The various operational components and subsystems in electronics portion 206 are connected together with conventional connectors.

The data from the scanning portion 203 is generally in the form of a stack of two dimensional image slices of a region of interest, which are provided from conventional spiral CT, MRI or US scanners. Central processing unit 209 converts the scanned 2D data to a 3D voxel data representation, in a manner known in the art, and stores the results in another portion of memory 211. Alternatively, the converted data can also be directly sent to interface unit 213 to be transferred to the virtual navigation terminal 216. The conversion of the 2D data could also take place at the virtual navigation terminal 216 after being transmitted from interface 213. Preferably, the converted data is transmitted over carrier 214 to the virtual navigation terminal 216 in order for an operator to perform the computer aided treatment planning. The data can also be transported in other conventional ways such as storing the data on a storage medium and physically transporting it to terminal 216 or by using satellite transmissions.

The scanned data need not be converted to its 3D representation until the visualization rendering engine requires it to be in 3D form. This may save computational steps and memory storage space.

Virtual interactive visualization terminal 216 includes a screen 217 for viewing the image data, an electronics portion 215 and interface device 219 such as a keyboard, mouse or track ball. The electronics portion 215 generally includes a interface port 221, a central processing unit 223, other components 227 necessary to run the terminal and a memory 225. The components in terminal 216 are connected together with conventional connectors. The converted voxel data is received in interface port 221 and stored in memory 225. The central processor unit 223 then assembles the 3D voxels into a virtual representation which can be displayed on screen 217. Preferably, a graphics accelerator which is optimized for volume rendering can also be used in generating the representations. The virtual interactive visualization terminal 216 can be embodied using a high speed graphics work station, such as manufactured by Silicon Graphics, Inc., or in a high speed personal computer, such as an IBM compatible computer with a Pentium III (or higher) processor having a 1 GHZ or faster clock speed.

The operator can use interface device 219 to interact with the system 200, such as to indicate which portion of the scanned body is desired to be explored. The interface device 219 can further be used to control the image being displayed, including the angle, size, rotation, navigational position and the like.

Scanning device 205 and terminal 216, or parts thereof, can be part of the same unit. Numerous CT, MM, and US systems are suitable for such applications. A single platform may be used to receive the scanned image data, convert the image data to 3D voxels if necessary and perform the guided navigation.

In many virtual visualization and surgical planning operations, the use and registration of multiple images is desirable. This can be the result of acquiring multiple sets of image data from a region over time, acquiring multiple image sets of a region using different patient orientations, or by acquiring multiple image sets of a region using various technologies to exploit the advantages of various imaging techniques. When multiple sets of image data are acquired, such image sets must by registered in some manner in order to reasonably use the data in each image set. Exact image registration, for example, a voxel specific registration process, can be very difficult to achieve and is processor intense. In many applications, such precise registration is not required.

Figure 3:
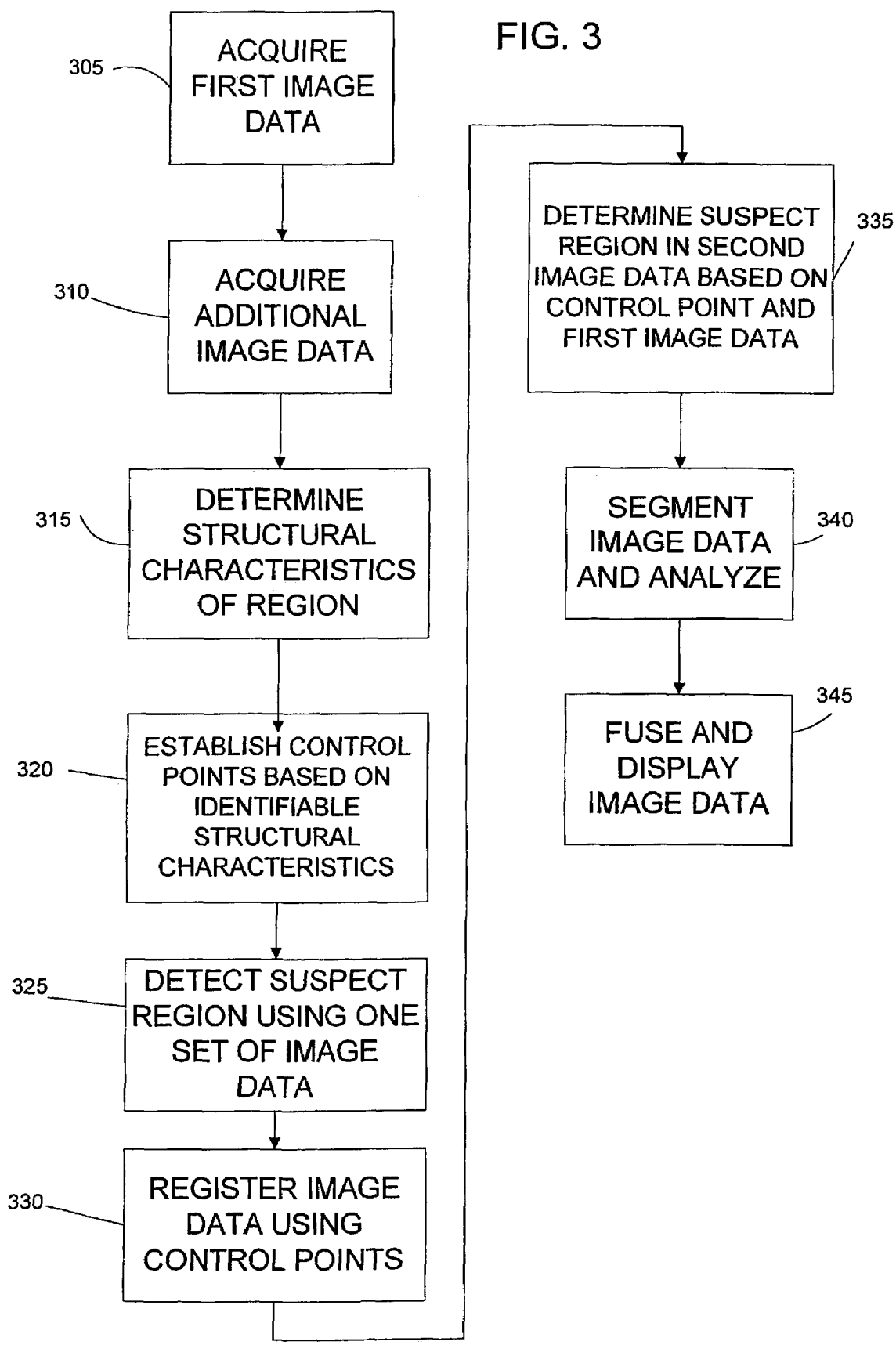
FIG. 3 is a flow diagram illustrating an overview of a flexible registration process for aligning multiple sets of image data, such as in multi-modality imaging and single-modality image series acquisition.

FIG. 3 is a flow diagram illustrating an overview of a flexible registration process for aligning multiple sets of image data, such as in a series of single-modality images and in multi-modality imaging which can be practiced using the system of FIG. 2 and variations thereof. This process will be described in connection with the visualization and analysis of plaque build up within a blood vessel, but is extendible into many forms of single-modality image sets, multi-modality imaging and other multiple image set registration applications. In step 305, a first set of image data is acquired. In the case of arterial stenosis, the first set of image data may be acquired using 3D time-of-flight magnetic resonance angiograpy (TOF MRA). The 3D TOF MRA has proven to be an effective imaging technique for providing good enhancement of the arterial lumen. Thus, the gross structure of the arterial lumen and the suspect location of a plaque build up can be identified using this imaging technique. However, TOF MRA does not provide optimal resolution at distinguishing the characteristics among soft tissues and the components of the plaque.

In step 310, a second set of image data is acquired. As noted above, this can be image data acquired at a different time, a different patient orientation or with a different imaging technology. In the case of arterial stenosis, a second imaging mode is used to provide a set of image data which can be segmented to distinguish characteristics of the soft tissue and plaque. For example, $T_1$-weighted MR imaging ($T_1$-MRI) has been found to provide good contrast and can be performed in the same MRI series as the TOF MRA. In order to obtain additional information, yet another set of image data can be acquired to provide features not easily distinguished in the previous image data sets. For example, MRI data does not readily distinguish a calcification component of the plaque. To properly determine the total volume and composition of the plaque, a CT image dataset of the region can also be acquired.

Using one set of the image data acquired in steps 305 and 310 the major structural characteristics of the region, including possible suspect regions, can be ascertained (step 315). As noted above, the TOF MRA image data provides a good rendering of the 3D arterial lumen and can be used to identify any regions of possible stenosis.

Figure 4:
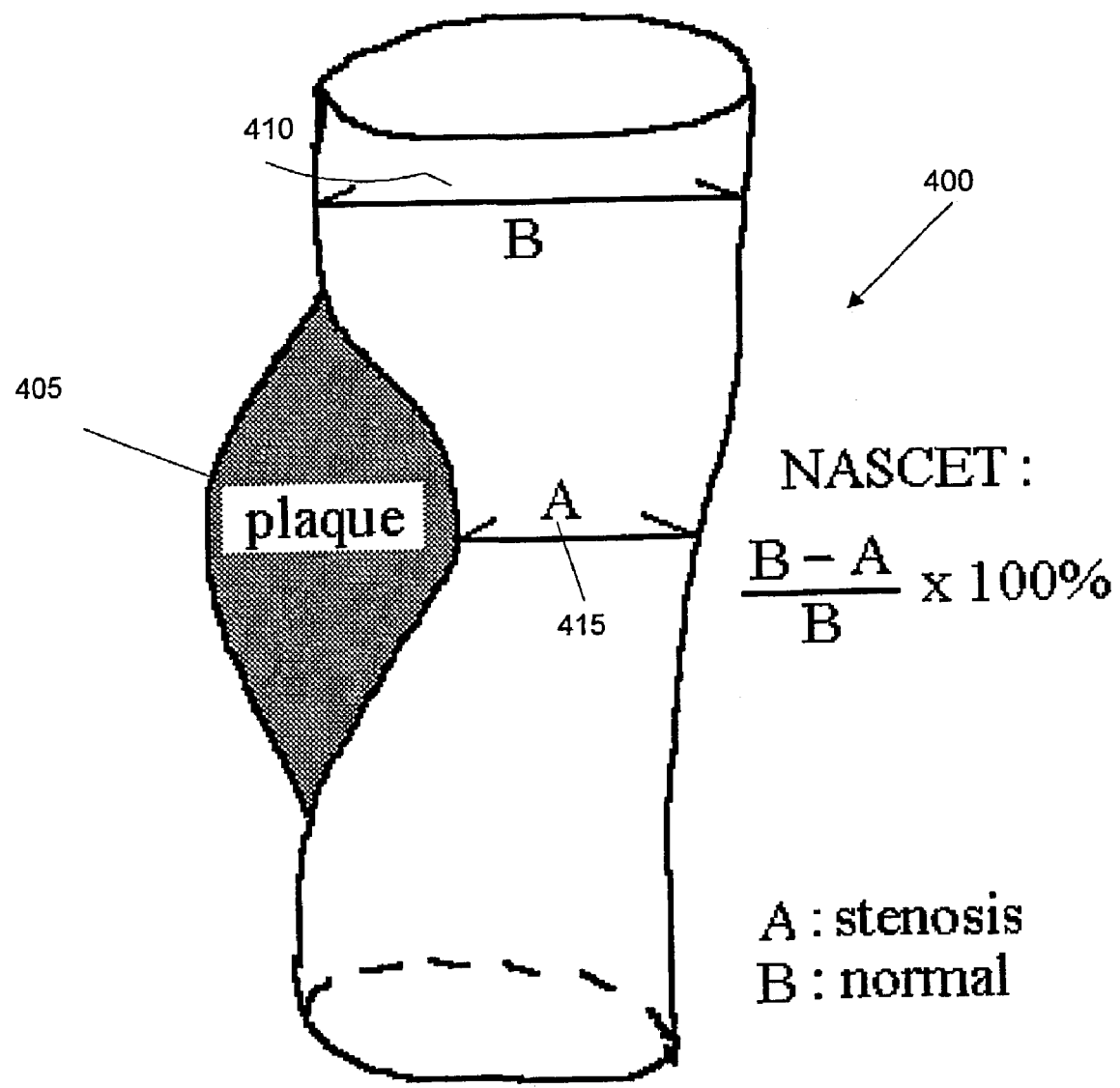
FIG. 4 is a pictorial diagram illustrating a section of a blood vessel with plaque build up resulting in stenosis.

FIG. 4 is a pictorial diagram illustrating a section of a blood vessel with plaque build up resulting in stenosis. The arterial lumen 400 is shown with a region of plaque 405 impinging on the lumen resulting in stenosis. The lumen can be characterized by a diameter of the normal vessel (B) 410 and a minimum diameter at the location of the stenosis (A) 415. The degree of stenosis can be characterized by the definition set forth by the North American Symptomatic Carotid Endarterectomy Trial (NASCET). The NASCET is determined as:

$$\frac{B-A}{B} \times 100\%$$

Figure 5:
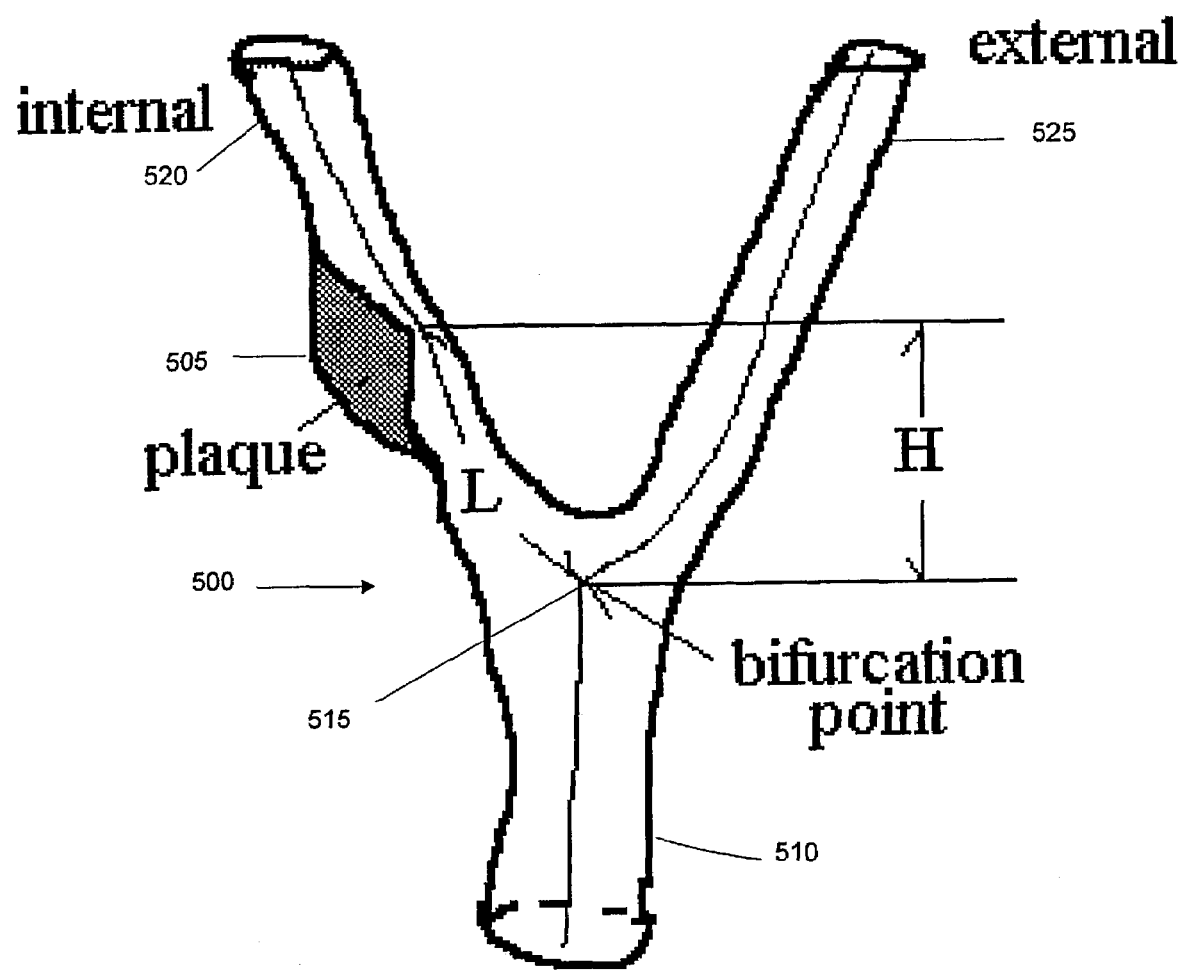
FIG. 5 is a pictorial diagram illustrating a branched section of a blood vessel with plaque build up resulting in stenosis, the branched section featuring a bifurcation point which can be used as a control point for image data registration.

FIG. 5 is a pictorial diagram illustrating a branched section of a blood vessel with plaque build up resulting in stenosis. From step 315, the lumen of the artery 505 can be extracted and the regions of possible stenosis 505 can be identified. In addition, a centerline skeleton of the arterial structure can also be determined. In FIG. 5, the artery exhibits a first arterial section 510 which branches at a bifurcation point 515 into an internal arterial branch 520 and an external arterial branch 525.

After at least one set of image data has been processed to determine the structural characteristics of the region (step 315), at least one control point is established using a consistently identifiable structural characteristic of the region (step 320). Referring to FIG. 5, in the case of a branched arterial structure, the bifurcation point 515 can be determined and selected as the control point for subsequent registration operations.

Figure 6:
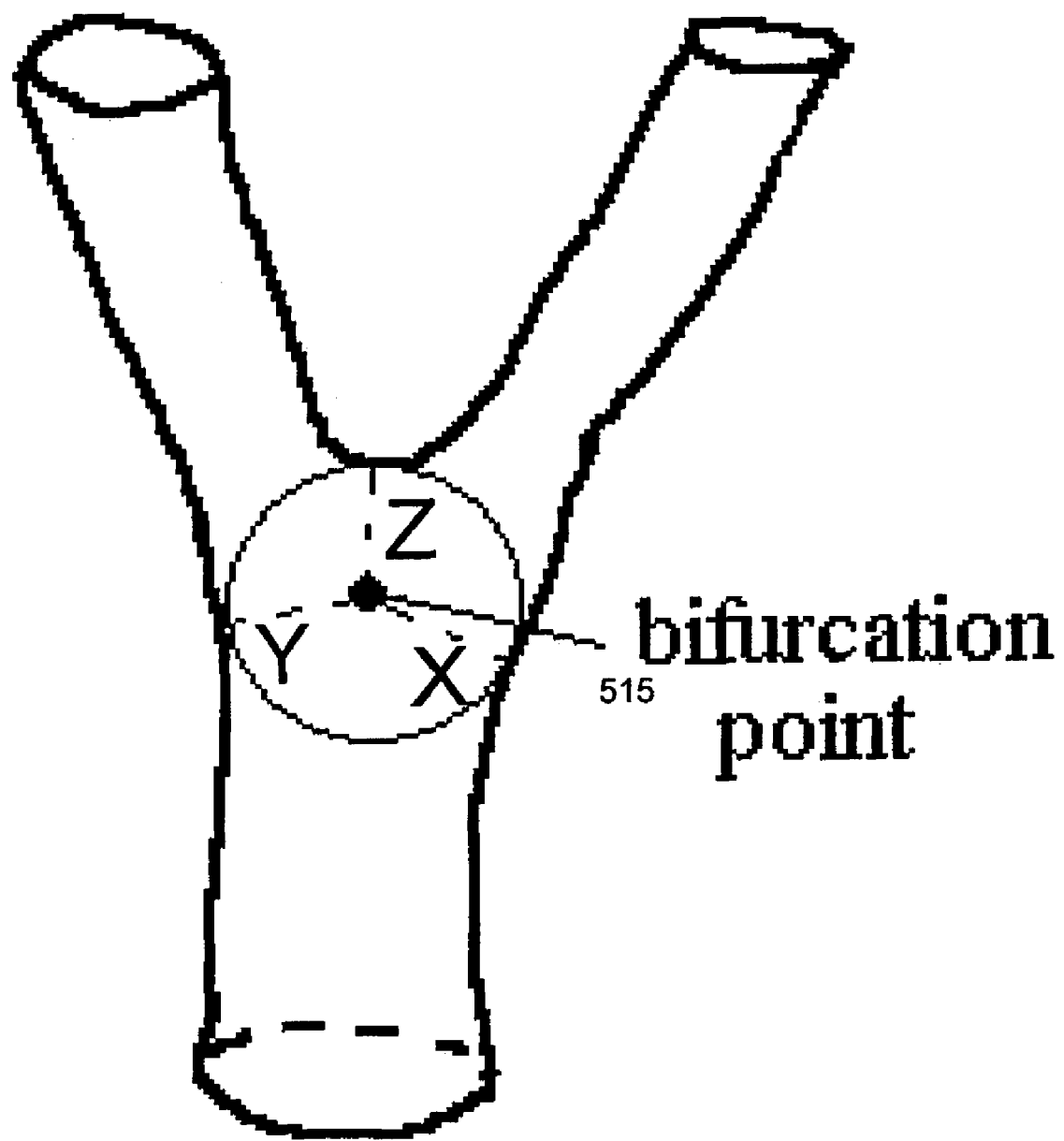
FIG. 6 is a pictorial diagram of a branched section of a blood vessel further illustrating the location of the bifurcation point which can be used as a control point for image data registration.

FIG. 6 is a pictorial diagram of a branched section of a blood vessel further illustrating the location of the bifurcation point which can be used as a control point for image data registration. From the skeletal centerline of the arterial lumen the bifurcation point can be determined. Referring to FIG. 6, the bifurcation point is refined as being the center of a maximal diameter sphere that fits within the lumen at the bifurcation region. Using the center of the maximal sphere as the origin, a coordinate system, such as X, Y and Z axes, can be defined in the region for subsequent registration. A number of different coordinate systems can be used. For example, a Cartesian coordinate system can be used which corresponds to the orientation of the human body being imaged, e.g., with the Z-axis aligned along the height of the body (e.g., from head to toe), the Y-axis oriented from back to front and the X axis running laterally (e.g., from left to right). The units of length for the coordinate system can be arbitrarily set to one voxel or some other convenient unit of measure. The absolute magnitude of the units used will vary based on the acquisition properties of the imaging scanner being used.

Figure 7A:
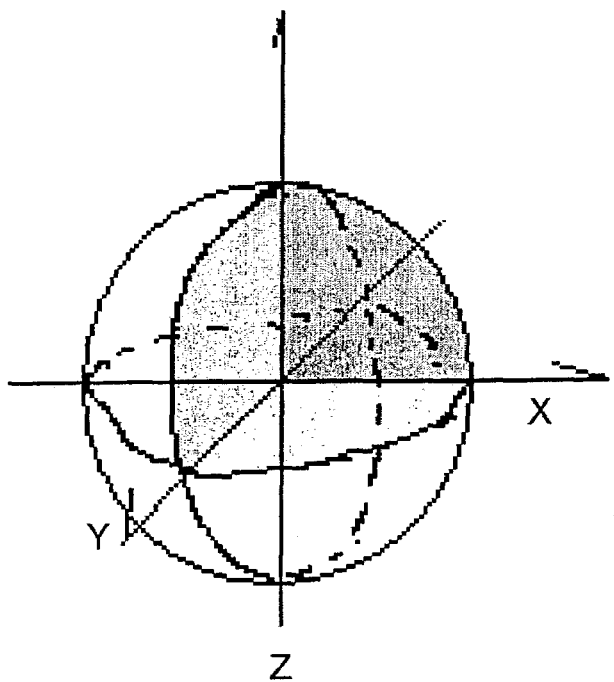
FIG. 7A further illustrates the determination of the control point for a spherical model.
Figure 7B:
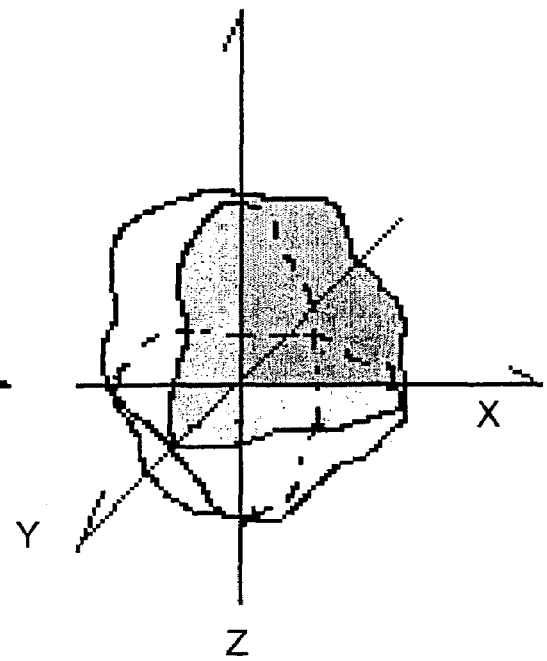
FIG. 7B illustrates the application of the control point and coordinate system of FIG. 7A as applied to a deformable model.

FIG. 7A further illustrates the determination of the control point and the registration between a spherical model and its deformable model. As illustrated in FIG. 7A, three mutually orthogonal planes aligned along a Cartesian coordinate system are defined which can readily be applied to a deformable model, such as that illustrated in FIG. 7B. The two coordinate systems can be registered by aligning them each to a reference coordinate system. The reference coordinate system can be one which is associated with anatomical axes of the human body. This flexibility allows registration of multiple image sets despite variations in resolution and other variables.

Returning to FIGS. 3 and 5, using the control point 515 and the structural characteristics of the region, the approximate location of suspect regions is determined in at least one of the sets of image data (step 325). In the case of carotid stenosis, the location of the suspect regions is determined by finding the areas of minimum diameter 530 in the lumen, which correspond to areas of maximum stenosis in a region of plaque. The location of the suspect region can be determined in a number of ways. For example, the curve length L from the control point 515 to the point of minimum diameter 530 along the skeletal centerline provides a first measure of location. In addition, the "vertical" distance H, which is measured along the imaginary Z-axis of the coordinate system framing the control point 515, can be used to determine the relative position of the suspect region with respect to the control point.

After the control point(s) and the position of suspect areas have been identified in a first image data set, registration of the first image data set with the additional image data sets can take place (step 330). The process of flexible registration entails identifying the control point(s) in each image data set and using the control points as a datum for registration of the image data sets. For example, in the example of a branched arterial structure discussed above, the bifurcation point would be located in each set of image data. In the case of $T_1$-weighted MR images, generally the bifurcation point is manually identified by a user of the system, such as a physician. The image data sets are registered to one another using the control point(s) and are aligned to the coordinate system which is assigned. Assuming an affine model of the region being imaged, three control points can be used to fully automatically register the coordinate systems of the image data sets in 3D space. With less than three control points, the registration process can be initially automated and then completed using manual intervention to optimize the registration process.

Using an appropriate transfer function, the voxels of the arterial lumen can be displayed as a translucent structure with the skeletal centerline therein. In addition, the suspect regions can be highlighted on the skeletal centerline by emphasizing the suspect regions, such as by using a different color to display suspect regions.

To determine the location of stenosis, the information from the first image data set, in this case the previously processed results of TOF MRA, are preferably used. The bifurcation point is detected in the $T_1$-weighted MR images, generally, manually by physician. The same coordinate system defined with respect to the first image data set is then applied to the $T_1$-weighted MR images. Starting at the control point, the vertical distance H is measured along the Z-axis to arrive at the position corresponding to the approximate location of the stenosis in the second set of image data (step 335). In the $T_1$-weighted MR images the vessel lumen is difficult to differentiate. However, if an imaging technology is employed which offers adequate delineation of the vessel lumen, the distance L along the center line of the lumen to the suspect region can also be used. Exact voxel accuracy of location is not necessary in aligning the images. The important criteria is that a suspect region in the image data covers the entire region of stenosis and plaque which has been identified in step 325.

Image segmentation can then be performed in the region of plaque to determine the nature and composition of the plaque build up (step 340). If the plaque has fatty components, those components will exhibit a higher intensity in the $T_1$-weighted MRI image as compared to both the vessel lumen and the vessel wall. Such components can be detected and identified in the segmentation results of the $T_1$-weighted MR images. The volume of the fatty components can be quantified and a 3D model of the plaque can be created.

As noted above, the TOF MRA data set provides good delineation of the lumen whereas the $T_1$-weighted MR data provides good segmentation results for the fatty components of the plaque causing the stenosis. By employing flexible image registration and then fusing the registered datasets into a single display data set, a single display providing the enhanced features of both the arterial structure and the plaque can be provided (step 345).

Image fusion can take on several forms but generally results in at least a portion of the features of each image set being presented simultaneously or at least selectively on a common display and in a common registration. Generally, each set of image data, whether multi-modality image data or a series of single-modality image data sets, is pre-processed through an image segmentation process. Image segmentation is used to emphasize and extract various features in the sets of image data. One or more sets of image data can be selected to display the raw image data. In the case of arterial imaging for carotid stenosis, this would generally by the TOF MRA image data or US image data which effectively delineates the arterial lumen. Segmented portions of the other image data sets can be simultaneously or selectively rendered on the display. Each of the sets of image data can be rendered as a layer in the display to effectively render the region of interest. For example, in viewing a region of stenosis, an operator can selectively heighten the image data from the $T_1$-weighted MR data to emphasize fatty components of the plaque or the CT image data to emphasize the calcification components of the plaque. The rendering can be performed initially in an automated manner than optimized by the user, generally by use of a GUI interface. In addition, the operator can generally navigate in the image data, change views, zoom, etc. The processing of the present method effects these navigation and manipulation commands on all fused image data sets such that all interaction is effected on all image models. This is possible because the sets of image data are registered to one or more common control points and are aligned to a common coordinate system.

The $T_1$-weighted MR data provides good segmentation results for the fatty components of the plaque but generally can not reliably distinguish the calcification components of the plaque. Generally, CT image data exhibits higher spatial resolution and better contrast between calcification and other tissues. Thus, it is desirable to scan the region with a CT scanner to acquire CT image data which can also be flexibly registered with the TOF MRA data set.

In the CT image data set, the vessel lumen and wall have similar intensity values as that of soft tissue. As a result, the arterial lumen is difficult to delineate in a CT image. A first approach to overcome this issue is to perform CT image scanning twice. In a first imaging scan, CT angiography (CTA) is acquired following the injection of a contrast agent in the blood. From the CTA image data, the carotid lumen will be delineated. The skeleton along the centerline of the lumen can be generated and the bifurcation point can then be determined. By tracing the skeleton up-stream the distance L, the stenosis location can be detected. The second CT imaging scan is acquired with the same scanning settings, but without the presence of the contrast agent. In the second scan, only calcification regions are depicted as regions of increased intensity. Since the field of view (FOV) and scanning setting are identical, the two scans are assumed to be registered at voxel-specific accuracy. The region of stenosis in the second scan is then considered to be the same as that in the CTA scan. Then, a suitable segmentation algorithm can be applied to the region of stenosis to extract the region of calcification. The volume of the calcification can be measured and a 3D model of it can be created.

Figure 10:
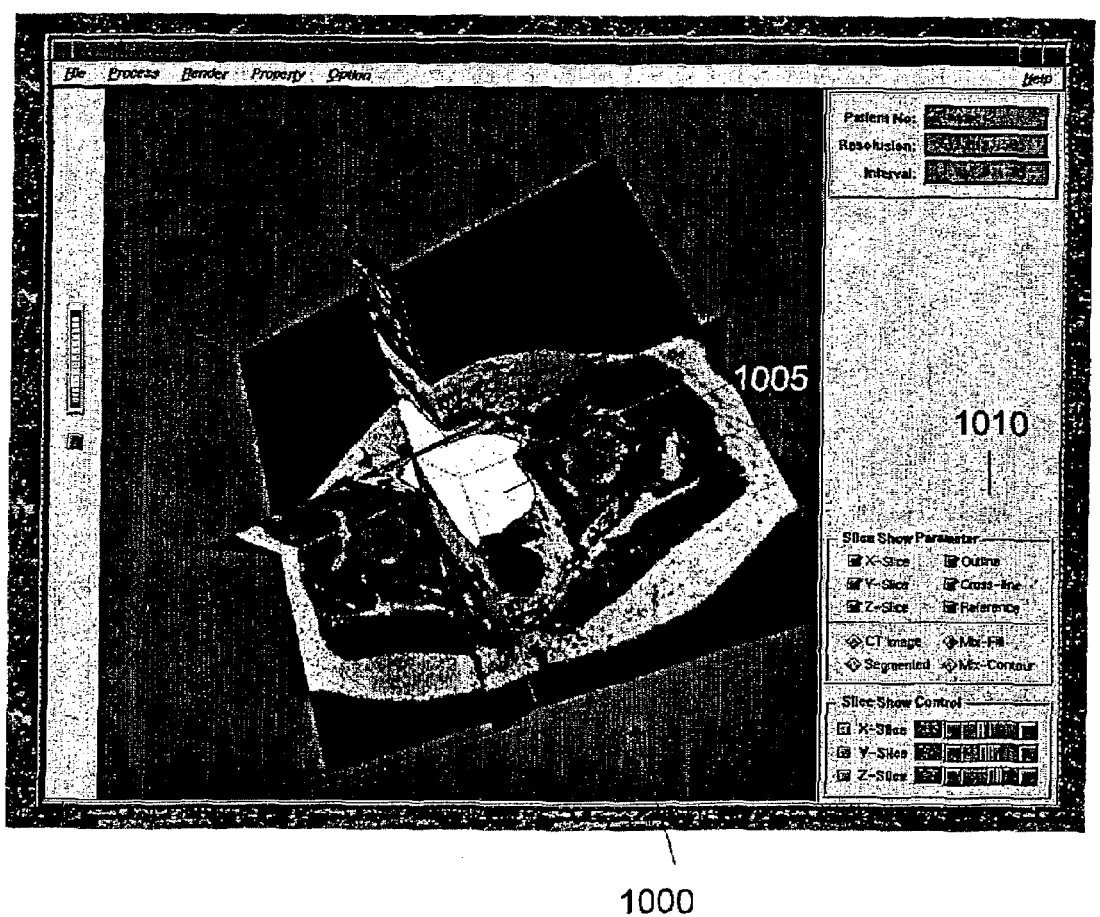
FIG. 10 is a pictorial diagram illustrating an exemplary graphical user interface display illustrating segmented multi-modality images after a fusion operation.

The second approach to using the CT imaging data to determine the regions of calcification does not use a CTA scan with a contrast agent. Instead, the stenosis region is detected manually in the CT images. This task is generally performed by a physician with help of image rendering tool. Various forms of image rendering tools are known in the art and generally provide a graphical user interface (GUI) which allows the user to readily manipulate both the individual image slices and the 3D virtual model on a computer screen. An example of one such GUI display is depicted in FIG. 10. Anatomical knowledge of the structure, such as the carotid artery, is generally used in this procedure.

FIG. 10 illustrates an exemplary GUI display of a fused display of a segmented object 1005 within the raw CT image data of the region of interest 1000, in this case the bladder of a patient. In the view depicted in FIG. 10, the image data is presented as a 3D body in 2D forms, i.e. the image is shown in cut away slices in two orthogonal directions and projecting in a third direction. The GUI includes on-screen controls 1010 which can be selected and modified using either a computer keyboard or digital pointer, such as a mouse, trackball and the like. Using the GUI the user can inspect details of the image, edit the segmentation results, change the view and the like.

After detecting a suspect region, such as an area of possible stenosis, the suspect region image is segmented and processed substantially as described above. While this second process requires further manual intervention, it does not require the use of a second CT scan or the use of a contrast agent.

While in the above example, TOF-MRA and CTA imaging were described as imaging methods to determine the arterial lumen, it will be appreciated that US imaging can also be used in place of one or both of these imaging techniques.

Determination of Likelihood of Rupture

The plaque which forms in the arterial lumen and results in stenosis is generally composed of blood volume, fatty components and calcification components. The total volume of the plaque can be obtained by summation of the volume of fatty components identified in the $T_1$-weighted MR image data whereas the calcification components can be determined from the segmented CT image data. The percentage of each component can be calculated. The larger the volume of blood or its percentage, the higher the probability of a rupture of the plaque, with increased attendant risk of stroke. In addition, a close proximity of blood deposits near the surface of the plaque build up also provides an indication of high risk of rupture. The level of risk is not quantifiable in absolute terms. However, by employing an arbitrary scale for both blood volume and surface depth, a weighted relative risk factor can be associated with the stenotic region. Based on such "risk scales," regions of risk can be highlighted, such as by use of one or more different display colors, to alert the user of the risk. The risk factor values can also be compared to predetermined or user defined threshold values, which if met or exceeded, would trigger more active alarm indications to the user.

The volume of the blood inside the plaque and its location near the boundary are two indicators for the likelihood of rupture. Therefore, accurate segmentation of the plaque components and identification of their spatial relation are objectives in stroke risk assessment. In the present systems and methods information from (1) CT/CTA (calcification), (2) TOF MRA or US(lumen), and (3) $T_1$-weighted MRI (fatty, blood, and others) images are simultaneously used to render this information. The information is represented together to show the tissue spatial relation in 3D space. This requires the use of both image registration and image segmentation computer processing techniques. Each of these operations benefit from a degree of user editing. The editing can be performed by displaying the segmented objects inside the raw image or by displaying all segmented objects together, as depicted in FIG. 10.

Figure 8:
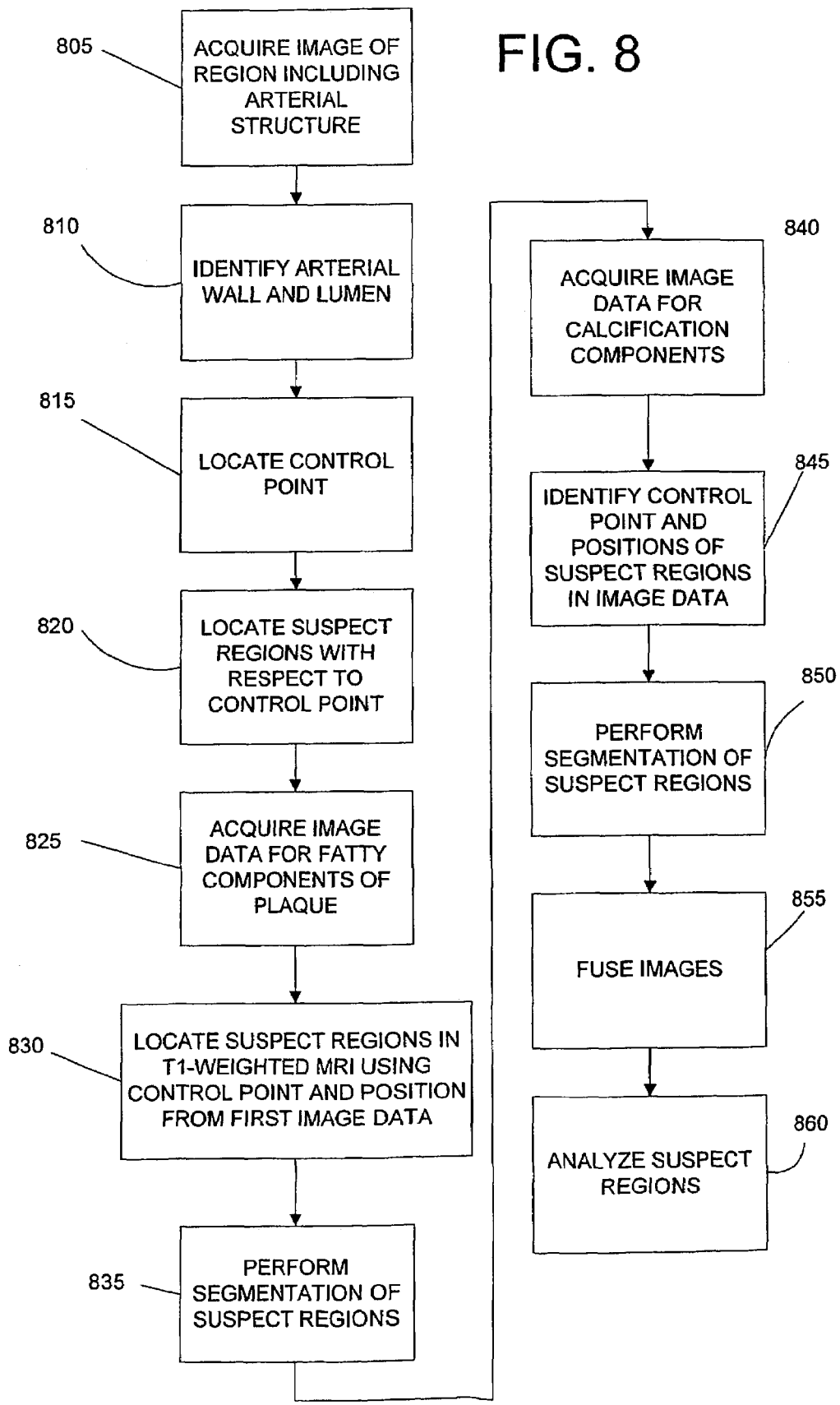
FIG. 8 is a flow diagram further illustrating the method of FIG. 3 as applied to a method of visualizing and analyzing carotid stenosis.

FIG. 8 is a flow chart summarizing the application of the method of FIG. 3 as specifically applied to the visualization and analysis of an arterial structure for carotid stenosis. In step 805 image data is acquired to visualize the arterial wall and lumen. This generally takes the form of TOF MRA or US image data. After image segmentation, the arterial wall and lumen are clearly distinguishable in the MRA or US image data (step 810). From the MRA image which illustrates the lumen, the centerlines of the lumen are calculated and the bifurcation point is located as the control point (step 815). Suspect regions are located in the lumen which may reflect areas of stenosis (step 820). The position of these suspect regions is then determined with respect to the control point and an arbitrary coordinate system which is defined around the control point.

In addition to the TOF MRA image data, a second set of image data is acquired to highlight fatty components within the suspect regions (step 825). Generally, a $T_1$-weighted MRI image data set has been found acceptable for this purpose. The control point and coordinate system which was defined in the first image data are then located and placed in the second image data set and the position of the suspect regions are located (step 830). Image segmentation is performed on the second image data set in the suspect regions to highlight the fatty components of the plaque deposits.

A third image data set is acquired to delineate the calcification components of the plaque deposits (step 840). This third image data set can take the form of CT image data. Within the third image data set, the control point and coordinate system are identified and placed and the position of the suspect regions are identified (step 845). Again, image segmentation in the suspect regions can then be performed to delineate the regions of calcification (step 850).

Using the control point and coordinate system which has been located in each set of image data, the sets of image data are registered with one another and fused into a single display image which can be presented on the display of the visualization system (step 855). Using the fused image, the user can readily analyze the suspect regions, for example to determine the volume and composition of any plaque deposits, the likelihood of rupture and the quality of the arterial surface for receiving a stent graft (step 860).

Spatial Inhomogeneity Correction

In MR image data, the inter-slice and intra-slice image data often contains spatial inhomogeneities which adversely affect automated analysis of these images. Correction for spatial intensity inhomogeneities in inter- and intra-slices provides improved results in automated quantitative analysis of MR images. The inhomogeneities locally alter image intensity mean, median, and variance. It is known that they vary over time and with different acquisition parameters and subjects. For virtual treatment planning, a general purpose correction algorithm that can work for any scanning protocol and anatomy region is desirable.

Figure 9:
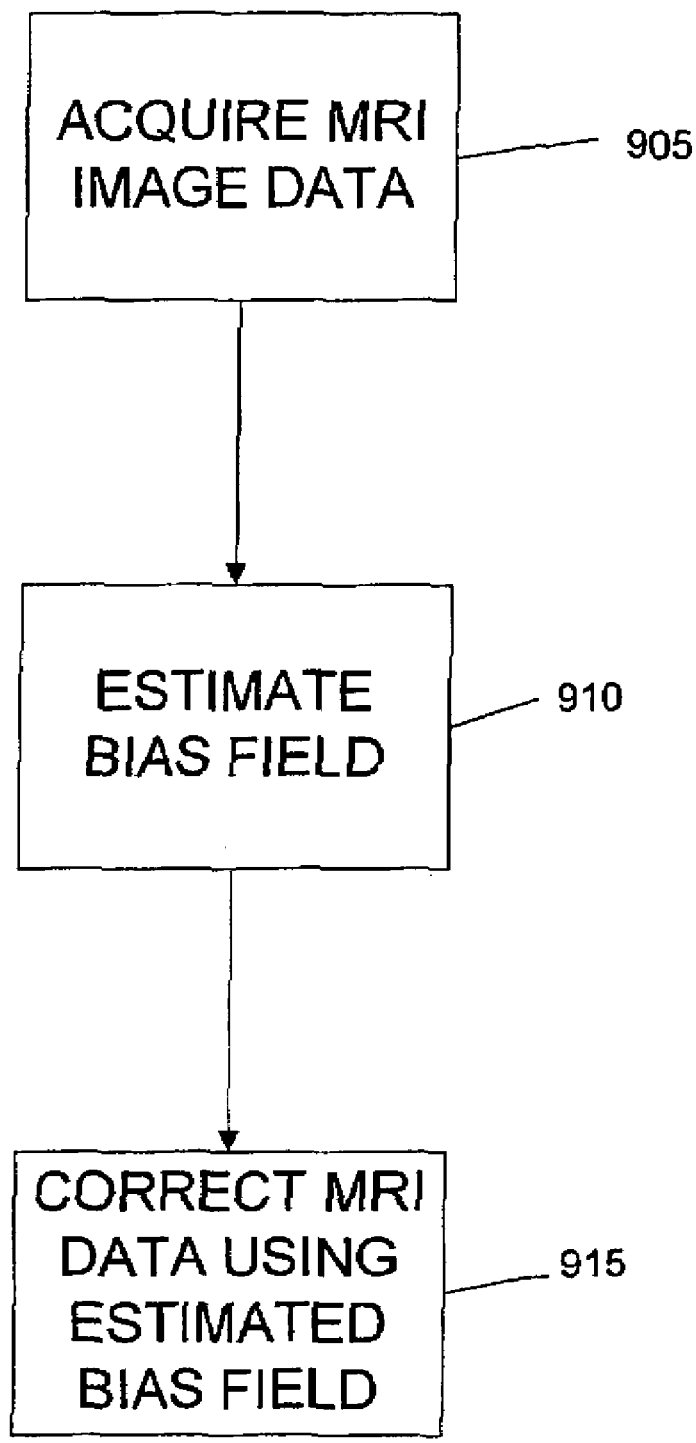
FIG. 9 is a flow diagram illustrating a process for correcting spatial inhomogenieties in MRI image data.

A correction method based on known renormalization group theory has now been found to be useful for the spatial inhomogeneity of MR image data. As illustrated in FIG. 9, following image data acquisition (step 905), the correction method consists of two primary steps. The first step is to estimate an inhomogenous bias field (step 910). The second step is to correct the MR image based on that bias field (step 915).

The notations which will be used in connection with the present renormalization transformation (RT) method for MR image are now presented. Let S be a single-connected, finite subset of the 2D integer lattice. One can consider S as the pixel locations of a region of interest (ROI) in a 2D image. Let $X=\{x_i: i \in S\}$ be an image, where $x_i$ is the intensity value of pixel i and it takes value within a finite set. Denote $\partial_i$ and $|\partial_i|$ as the first order neighborhood of the pixel i and the number of pixels inside this neighborhood (pixel i itself is also a member of this neighbor). The RT is defined as:

$$T(X) = \left\{y_i : y_i \equiv \frac{\sum_{k \in \partial_i \cap S} x_k}{|\partial_i \cap S|}, i \in S\right\}. \quad 2.1$$

T(X) is a new image with the same pixel location and its intensity value of each voxel is the average intensity of those of pixels in its neighborhood. The RT is a linear transformation and can be calculated locally. This makes it possible for a fast parallel implementation.

The estimation of the bias field is to apply RT iteratively to the MR image X. When the condition $$\max_{i \in S} | T^{(n)}(X)_i - T^{(n+1)}(X)_i | \leq t \qquad 5$$

is satisfied, $T^{(n)}(X)$ is the estimation of the bias field, where n is the number of iteration and t is a pre-set threshold. For example, we can set t as the average intensity of the image X dividing by 3000.

The bias field is often modeled as the following classical way:

$$Y = X \cdot f + n \qquad 2.2$$

where Y is the obtained MR image, X is the ideal image without inhomogeneity, f is the bias field, and n is the noise. Ignoring the noise component, the image data is the multiplication of the ideal image and the bias field. Following this model, the correction procedure can be performed by dividing the image data by the estimated inhomogeneity bias field. However, in the RT model, the RT is a linear transformation rather than a multiplication transformation. Therefore, the following model is more accurate for RT method:

$$Y = X + f + n \qquad 2.3$$

Where Y, X, n, and f were defined above. For correction algorithms ignoring the noise, we induce the following model:

$$X = Y + \alpha \cdot (\hat{f} - M_0) \qquad 2.4$$

where $\alpha(\hat{f} - M_0)$ is a linear transform applied on the estimated bias field $\hat{f}$, $\alpha$ is a scaling factor and $M_0$ is an image calculated from X. This model assumes that all pixels represent a common tissue type. In practical situations, however, this is not the case. Hence, a correction model is applied in a flexible way to ensure that the assumption is satisfied to the greatest degree possible. For example, the image can be processed on a row by row or column by column basis. Alternatively, image segmentation can be performed initially and regions of substantially common tissue types can be delineated and separately processed by applying the model to each region. The determination of $\alpha$ and $M_0$ should also be adaptive to the practical situation. For example, we can set $\alpha = -1$ and compute $M_0$ as the average intensity of the image.

Image Segmentation

A difficulty encountered in imaging is that several of the relevant anatomical structures have similar intensity values on the CT image. This can make it difficult to distinguish the various structures which overlap or are interrelated. To address this problem, a two-level image segmentation process can be employed. The two-level segmentation process involves low-level processing of the voxels in the region of interest followed by high-level organ extraction. During the low-level processing, the voxels of the 3D dataset are clustered into groups based on an intensity feature of the voxels, which can be measured by an associated local intensity value vector. This can be determined using a modified self-adaptive on-line vector quantization algorithm, such as is described in the article "A self-adaptive on-line vector quantization algorithm for MRI segmentation," by Chen et al. in the proceedings of The 7th Scientific Meeting of ISMRM, May 1999, Philadelphia, which is hereby incorporated by reference. In the low-level classification, each voxel is associated with a local vector which is defined in 3D space. From the local vectors, a feature vector series can be derived using a components analysis which is well known in the art. The feature vectors are then clustered using a self-adaptive on-line vector quantization algorithm. The voxels are then grouped according to the classification of their feature vectors and are assigned an integer value representing this classification.

After the low-level processing is complete, the high level organ extraction processing can follow. Initially, a user locates a seed, or starting point, within regions representative of soft tissue, bone and air spaces. The system then applies a region growing algorithm starting from the seed points to extract the anatomical features of the region.

Bone structure, which presents different contrast compared to the surrounding tissues is fairly easy to automatically segment. However, certain structures may require additional user input to fully delineate these structures. For example, the soft tissue of the inner ear presents a similar intensity value on CT images as compared to the surrounding soft tissue. Thus, to insure proper extraction of such features, it may be desirable for the user to manually delineate the outline of the structure by manually tracing the contour on one or more of the image slices.

While the above described two level image segmentation is preferred, any method which provides accurate delineation of the neighboring structures in a region of interest can be used in the practice of the present treatment planning method. One such technique is described in the article "On segmentation of colon lumen for virtual colonoscopy" by Liang et al., Proceedings of SPIE Medical Imaging, pp 270-278, February 1999, San Diego.

Once image segmentation is performed, 3D image generation can be performed for each of the segmented objects using a number of known techniques, such as the Marching Cubes algorithm, which reconstructs the outer polygonal surface. However, because of the complexity of many anatomical structures, interactive rendering of all polygons in the display for each change to a portion of the display is processor intense and unduly costly. As more colors and surfaces are delineated in the displayed image, this burden increases. To minimize the processing overhead, the volume image dataset can be stored in a partitioned data structure, such as a binary space-partitioning (BSP) tree, in which the large dataset is parsed into relatively small portions which are stored in leaf nodes of the data structure. By identifying which leaf nodes are effected by any given operation, and only performing operations, such as Constructive Solid Geometry (CSG) operations, on the effected leaf nodes, the processing burden for interactive operations can be significantly reduced. As will be set forth in more detail below, the processing burden can be further reduced by use of a level of detail (LOD) rendering mode and/or a wavelet transformation to reduce the data volume.

As noted above, when a large dataset is involved, it may be required, or at least desirable, to reduce the size of the dataset to speed up processing and reduce processing cost. Noting that the tree structure can be preserved within a range of scales, the large volume can be shrunk to a smaller scale space for structure analysis.

A shrinking method based on multiresolution analysis theory can be used. The input data is the stack of binary images of the same size which can be obtained from the segmentation results of the CT or MRI scan. The x-direction is taken along the slice image width, the y-direction is along the slice image height, and the z-direction is along the direction of slice by slice. The foreground voxels in the tree volume are set to value of 128 (maximum) and the background voxels are set to value 0 (minimum). A Daubechies' bi-orthogonal wavelet transform with all rational coefficients can be employed. This one-dimensional (1D) discrete wavelet transformation (DWT) is first applied along to the x-direction row by row. From application of the DWT only the lower frequency components are retained and packed. The computation is preferably implemented in floating points. Noting that the DWT is applied to the binary signal, there are two kinds of nonzero coefficients which result in the lower frequency component. The first is of value 128 and this kind of coefficient is located in the interior of the volume. The second is of a value not equal to 128 and these coefficients locate the boundary of the volume.

The coefficients of the second kind are compared against a predetermined threshold value. If the absolute value of the coefficients is larger than a pre-set threshold T1, the value of the coefficient is set to 128; otherwise, it is set to 0. This results in a stack of binary images with a row size of half of the original dataset. The same DWT is then applied to the resulting dataset along the y-direction column by column, where the similar thresholding is employed to the lower frequency components. The result is again a stack of binary images, but now with both half row and column size as compared to the original dataset. Finally, the DWT is applied to the last result along the z-direction and the lower frequency components are retained. This step completes the first level decomposition.

The resulting dataset of the first level decomposition is of half size in all three directions as compared to the original dataset. If the shrinking procedure stops at this level, the finial thresholding is applied. It revalues those coefficients of nonzero and non-128 value. If the absolute value of this kind of coefficient is larger than a pre-set threshold T2, it will be revalued as 128; otherwise, it is revalued as 0. If further shrinking is needed, the same thresholding algorithm is applied with the threshold T1. Further shrinking proceeds as previously described, but is applied to the dataset shrunk at the last previous level. The decomposition procedure can be recursively applied until the resulting volume meets the desired reduced data volume. In the case where the slice images are of 512×512 pixel size, the maximum decomposition level is usually three, resulting in a 64×64 reduced pixel size.

The volume is isotropically shrank in all directions with the presented method. The two pre-set thresholds, T1 and T2, are used to control the degree of shrinking. If the volume is significantly over shrunk, connectivity may be lost in the reduced volume. If it is over shrunk to a lesser degree, two separate branches may merge into one branch in the reduced volume dataset. The larger the two threshold values, the thinner the reduced volume is. The range of those two thresholds is [0, r×128], where 0<r<1. Preferably, the range for virtual endoscopy is $r \in (0.08, 0.28)$ for T1 and $r \in (0.7, 0.98)$ for T2. The exact determination is dependant on the feature size of the particular application and is selected to achieve reduction while retaining the fidelity of the structure information in the shrunk volume.

The flexible image registration techniques and spatial inhomogeneity corrections are applicable to surgical planning processes. For example, in the case of angioplasty, the surgeon inserts a catheter into an occluded artery and inflates a balloon at the end of the catheter to force the occluded artery open and to expand a stent which maintains the opening. While this has become a common procedure, it is not without risk. For example, the arterial occlusion is generally related to a build up of plaque and fatty deposits on the arterial wall. If a portion of these deposits are dislodged during the angioplasty process or if the region of plaque ruptures, there is a risk of stroke and other complications. Using the present method of treatment planning, the artery can be imaged and, through image segmentation, the quantity and nature of the plaque deposits can be determined. The severity of the occlusion can be viewed by the surgeon who can navigate in the 3D image within the artery. A virtual intervention can then be performed, i.e., placing a virtual catheter within the arterial volume and expanding a virtual stent, and the results observed. If problems are observed, such as a high risk of rupture, the user can then alter the course of treatment to minimize the risk. The virtual catheter and stent require a dynamic model that conforms to the contours of the interior surface of the arterial wall. Such a model is analogous to the force field model previously used in guiding a virtual camera along a fly path in performing virtual colonoscopy.

Known volume rendering techniques use one or more defined transfer functions to map different ranges of sample values of the original volume data to different colors, opacities and other displayable parameters for navigation and viewing. During navigation, the selected transfer function generally assigns maximum opacity to the wall of the object being viewed. However, once a suspicious area is detected during virtual examination, a user, such as a physician, can interactively change the transfer function assigned during the volume rendering procedure such that the outer surface being viewed becomes substantially transparent, allowing the interior structure of the region to be viewed. Using a number of predetermined transfer functions, the suspicious area can be viewed at a number of different depths, with varying degrees of opacity assigned throughout the process. In addition, the shape of the region and texture of the region undergoing virtual examination can be analyzed to determine the nature of the region, such as a likelihood of cancerous tissue residing in a region being biopsied.

Although the present invention has been described in connection with specific exemplary embodiments, it should be understood that various changes, substitutions and alterations can be made to the disclosed embodiments without departing from the spirit and scope of the invention as set forth in the appended claims.

The invention claimed is:

1. A computer based method of visualizing a region using multiple image data sets comprising:
   acquiring first volumetric image data of a region;
   acquiring at least second volumetric image data of the region;
   determining structural features of the region using the first volumetric image data
   determining at least one control point in the region using at least one structural feature in the first volumetric image data;
   identifying the at least one control point in the region in the at least second image data of the region;
   registering the first image data and the at least second image data using said at least one control point;
   fusing the registered first image data and at least second image data into a common display data set; and
   wherein the region includes a branched structure having a common section and at least two branches extending from the common section forming a bifurcation region and wherein a bifurcation point is determined as the center of an imaginary maximal diameter sphere which is fit within the bifurcation region.

2. The method of visualizing a region using multiple image data sets of claim 1, wherein the branched structure is a blood vessel.

3. The method of visualizing a region using multiple image data sets of claim 1, wherein the at least second volumetric image data is acquired using a mode which is different from a mode used to acquire the first volumetric image data.

4. The method of visualizing a region using multiple image data sets of claim 3, wherein the mode used to acquire the at least second image data is selected to provide complimentary imaging characteristics to the mode used to acquire the first image data.

5. The method of visualizing a region using multiple image data sets of claim 1 wherein the second volumetric image data is acquired at a substantially different time from said first volumetric image data.

6. The method of visualizing a region using multiple image data sets of claim 1, wherein the second volumetric image data is acquired with the patient in an orientation which is different than an orientation used during acquisition of the first volumetric image data.

7. A method of visualizing and analyzing a region of artery comprising:
   acquiring first volumetric image data of a region of artery using a first acquisition mode;
   acquiring at least second volumetric image data of the region of artery using a second acquisition mode, said second acquisition mode being different than the first acquisition mode;
   determining structural features of the artery using the first volumetric image data;
   determining a bifurcation point in the artery using the first volumetric image data, the bifurcation point being the center of an imaginary maximal diameter sphere inscribed within a bifurcation region of the artery;
   defining a coordinate system with the bifurcation point as the origin;
   identifying the bifurcation point in the artery in the at least second image data of the region and applying the defined coordinate system to the at least second volumetric image data;
   registering the first volumetric image data and the at least second volumetric image data using the bifurcation point and coordinate system; and
   fusing the registered first volumetric image data and at least volumetric second image data into a common display data set.

8. The method of visualizing and analyzing a region of artery of claim 7, wherein the structural features include at least one region of stenosis resulting at least in part from a plaque deposit, and wherein the method further comprises the steps:
   identifying the location of the at least one region of stenosis in the first volumetric image data;
   using the location from the first volumetric image data, determining the location of the stenosis in the at least second volumetric image data.

9. The method of visualizing and analyzing a region of artery of claim 8, wherein the step of identifying the location of the at least one region of stenosis includes measuring the distance along at least one axis of the coordinate system from the bifurcation point to a point in the region of stenosis.

10. The method of visualizing and analyzing a region of artery of claim 8, wherein the at least second acquisition mode is selected to delineate fatty components of the plaque deposits.

11. The method of visualizing and analyzing a region of artery of claim 8, wherein the at least second acquisition mode is selected to delineate calcification components of the plaque deposits.

12. The method of visualizing and analyzing a region of artery of claim 8, wherein the at least second acquisition mode includes second and third acquisition modes, at least one of the second and third acquisition modes being selected to delineate fatty components of plaque deposits and at least one of the second and third acquisition modes being selected to delineate calcification components of plaque deposits.

13. The method of visualizing and analyzing a region of artery of claim 12, wherein the first acquisition mode is Magnetic Resonance Angiograpy.

14. The method of visualizing and analyzing a region of artery of claim 12, wherein the first acquisition mode is ultrasound imaging.

15. The method of visualizing and analyzing a region of artery of claim 12, wherein the second acquisition mode is $T_1$-weighted MR imaging.

16. The method of visualizing and analyzing a region of artery of claim 12, wherein the second acquisition mode is $T_2$-weighted MR imaging.

17. The method of visualizing and analyzing a region of artery of claim 12, wherein the first acquisition mode is time-of-flight Magnetic Resonance Angiograpy, the second acquisition mode is T1-weighted MRI imaging, and the third acquisition mode is Computed Tomography imaging.

18. The method of visualizing and analyzing a region of artery of claim 7, further comprising analyzing a plaque deposit identified in the fused image data.

19. The method of visualizing and analyzing a region of artery of claim 18, wherein the analyzing step includes determining the composition of the plaque deposit.

20. The method of visualizing and analyzing a region of artery of claim 19, wherein the analyzing step includes determining the volume and position of fatty components in the plaque deposit.

21. The method of visualizing and analyzing a region of artery of claim 19, wherein the analyzing step includes determining the volume and position of calcification components in the plaque deposit.

22. The method of visualizing and analyzing a region of artery of claim 19, wherein the analyzing step includes determining the volume and position of blood components in the plaque deposit.

23. The method of visualizing and analyzing a region of artery of claim 18, wherein the analyzing step further comprises assessing the risk of rupture of the plaque deposit.

* * * * *

UNITED STATES PATENT AND TRADEMARK OFFICE
CERTIFICATE OF CORRECTION

PATENT NO. : 7,356,367 B2 Page 1 of 1
APPLICATION NO. : 10/297349
DATED : April 8, 2008
INVENTOR(S) : Zhengrong Liang et al.

It is certified that error appears in the above-identified patent and that said Letters Patent is hereby corrected as shown below:

In "Government Interests"

Reads
"The invention disclosed herein was made with Government support under NIH Grant CA 79180. Accordlingly, the U.S. Goverment may have certain rights in this invention."

Should Read
--The invention was made with government support under grant number CA079180 awarded by the National Institute of Health. The goverment has certain rights in the invention.--

Signed and Sealed this

Nineteenth Day of August, 2008

JON W. DUDAS
*Director of the United States Patent and Trademark Office*